(12) United States Patent
Govari

(10) Patent No.: US 11,790,543 B2
(45) Date of Patent: *Oct. 17, 2023

(54) REGISTRATION OF AN IMAGE WITH A TRACKING SYSTEM

(71) Applicant: Biosense Webster (Israel) Ltd., Yokneam (IL)

(72) Inventor: Assaf Govari, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 0 days.

This patent is subject to a terminal disclaimer.

(21) Appl. No.: 17/985,192

(22) Filed: Nov. 11, 2022

(65) Prior Publication Data

US 2023/0102908 A1 Mar. 30, 2023

Related U.S. Application Data

(63) Continuation of application No. 16/704,042, filed on Dec. 5, 2019, now Pat. No. 11,527,002.

(51) Int. Cl.
*G06T 7/33* (2017.01)
*A61B 34/20* (2016.01)
(Continued)

(52) U.S. Cl.
CPC .............. *G06T 7/337* (2017.01); *A61B 34/20* (2016.02); *G06F 3/0482* (2013.01);
(Continued)

(58) Field of Classification Search
CPC ......... G06T 7/337; G06T 3/0068; G06T 7/32; G06T 11/00; G06T 2210/41; A61B 34/20;
(Continued)

(56) References Cited

U.S. PATENT DOCUMENTS 11,007,036 B2 * 5/2021 Pokotilov ................ A61C 7/08
2016/0249879 A1 * 9/2016 Mauldin, Jr. ........ A61B 8/5223
600/437

OTHER PUBLICATIONS

Kim M, Yun J, Cho Y, Shin K, Jang R, Bae HJ, Kim N. Deep Learning in Medical Imaging. Neurospine. Dec. 2019;16(4):657-668. doi: 10.14245/ns.1938396.198. Epub Dec. 31, 2019. Erratum in: Neurospine. Jun. 2020;17(2):471-472. PMID: 31905454; PMCID: PMC6945006. (Year: 2019).*

* cited by examiner

*Primary Examiner* — Neil R McLean
(74) *Attorney, Agent, or Firm* — Frost Brown Todd LLP

(57) ABSTRACT

A medical apparatus includes a registration tool, which includes a position sensor, A position-tracking system is configured to acquire position coordinates of the sensor in a first frame of reference defined by the position-tracking system. A processing unit is configured to receive 3D image data with respect to the body of the patient in a second frame of reference, to generate a 2D image of the surface of the patient based on the 3D image data, to render the 2D image to a display screen, and to superimpose onto the 2D image icons indicating locations of respective landmarks. The processing unit receives the position coordinates acquired by the position-tracking system while the registration tool contacts the locations on the patient corresponding to the icons on the display, and registers the first and second frames of reference by comparing the position coordinates to the three-dimensional image data.

20 Claims, 3 Drawing Sheets

(51) Int. Cl.
*G06T 7/32* (2017.01)
*G06F 3/04817* (2022.01)
*G06F 3/0482* (2013.01)
*G06T 3/00* (2006.01)
*G06T 11/00* (2006.01)

(52) U.S. Cl.
CPC ........ *G06F 3/04817* (2013.01); *G06T 3/0068* (2013.01); *G06T 7/32* (2017.01); *G06T 11/00* (2013.01); *A61B 2034/2051* (2016.02); *A61B 2034/2065* (2016.02); *G06T 2210/41* (2013.01)

(58) Field of Classification Search
CPC .... A61B 2034/2051; A61B 2034/2065; A61B 2034/2068; A61B 2034/2072; G06F 3/04817; G06F 3/0482
USPC ........................................................ 382/128
See application file for complete search history.

REGISTRATION OF AN IMAGE WITH A TRACKING SYSTEM

This application is a continuation of U.S. patent application Ser. No. 16/704,042, entitled "Registration of an Image with a Tracking System," filed Dec. 5, 2019, and issued as U.S. Pat. No. 11,527,002 on Dec. 13, 2022.

FIELD OF THE INVENTION

The present invention relates generally to registration of images, and specifically to images generated with different modalities that may be used for image-guided surgery.

BACKGROUND

In image-guided surgery a medical practitioner uses instruments that are tracked in real time so that positions and/or orientations of the instruments may be presented on images of a patient's anatomy during a surgical procedure. In some cases both the tracking and the imaging of the patient's anatomy may be implemented by one modality, such as fluoroscopy. However, because fluoroscopy uses ionizing radiation, its use should be minimized. Consequently in many scenarios an image of the patient is prepared in one modality, such as magnetic resonance imaging (MRI) or computerized tomography (CT) fluoroscopy, and the instrument tracking uses a different modality, such as magnetic tracking.

SUMMARY

Embodiments of the present invention that are described hereinbelow provide improved methods for registration of images with a tracking system, as well as systems and software implementing such methods.

There is therefore provided, in accordance with an embodiment of the present invention, a medical apparatus, which includes a registration tool, which includes a position sensor and is configured to be brought into contact with a surface of a part of a body of a patient. A position-tracking system is configured to acquire position coordinates of the position sensor in a first frame of reference defined by the position-tracking system in a vicinity of the part of the body of the patient, and a display screen. The apparatus further includes a processing unit, which is configured to receive three-dimensional (3D) image data with respect to at least the part of the body of the patient in a second frame of reference, to generate a two-dimensional (2D) image of the surface of the part of the body of the patient based on the 3D image data, and to render the 2D image to the display screen. The processing unit is further configured to superimpose onto the displayed 2D image a plurality of icons indicating locations of respective landmarks on the surface of the part of the body, to receive the position coordinates acquired by the position-tracking system while the registration tool contacts the locations on the surface of the part of the body of the patient corresponding to the icons on the display, and to register the first and second frames of reference by comparing the position coordinates to the corresponding locations in the three-dimensional image data.

In a disclosed embodiment, the position-tracking system includes a magnetic position-tracking system.

In another embodiment, the three-dimensional image data includes data from a computerized tomography (CT) system. Alternatively, the three-dimensional image data includes data from a magnetic resonance imaging (MRI) system.

In a further embodiment, the part of the body of the patient includes a head of the patient, and the 2D image shows a face of the patient.

In another embodiment, registering the first and second frames of reference includes applying relative scaling, rotations and translations between the first and second frames of reference so as to maximize a correlation between the position coordinates and the corresponding locations in the three-dimensional image data.

In yet another embodiment, the processing unit receives the landmark locations from a user marking the locations on the 2D image.

In still another embodiment, the processing unit is configured to track and display a location of an invasive probe inside the part of the body using the registered frames of reference.

There is also provided, in accordance with an embodiment of the present invention, a method for registering medical images. The method includes acquiring position coordinates of a position sensor in a registration tool in a first frame of reference defined by a position-tracking system in a vicinity of a part of a body of a patient as the registration tool is brought into contact with a surface of the part of the body, receiving three-dimensional (3D) image data with respect to at least the part of the body of the patient in a second frame of reference, generating a two-dimensional (2D) image of the surface of the part of the body of the patient based on the 3D image data, and rendering the 2D image to a display screen. The method further includes superimposing onto the displayed 2D image a plurality of icons indicating locations of respective landmarks on the surface of the part of the body, receiving the position coordinates acquired by the position-tracking system while the registration tool contacts the locations on the surface of the part of the body of the patient corresponding to the icons on the display, and registering the first and second frames of reference by comparing the position coordinates to the corresponding locations in the three-dimensional image data.

The present invention will be more fully understood from the following detailed description of the embodiments thereof, taken together with the drawings in which:

DETAILED DESCRIPTION OF EMBODIMENTS

Overview

Figure 1:
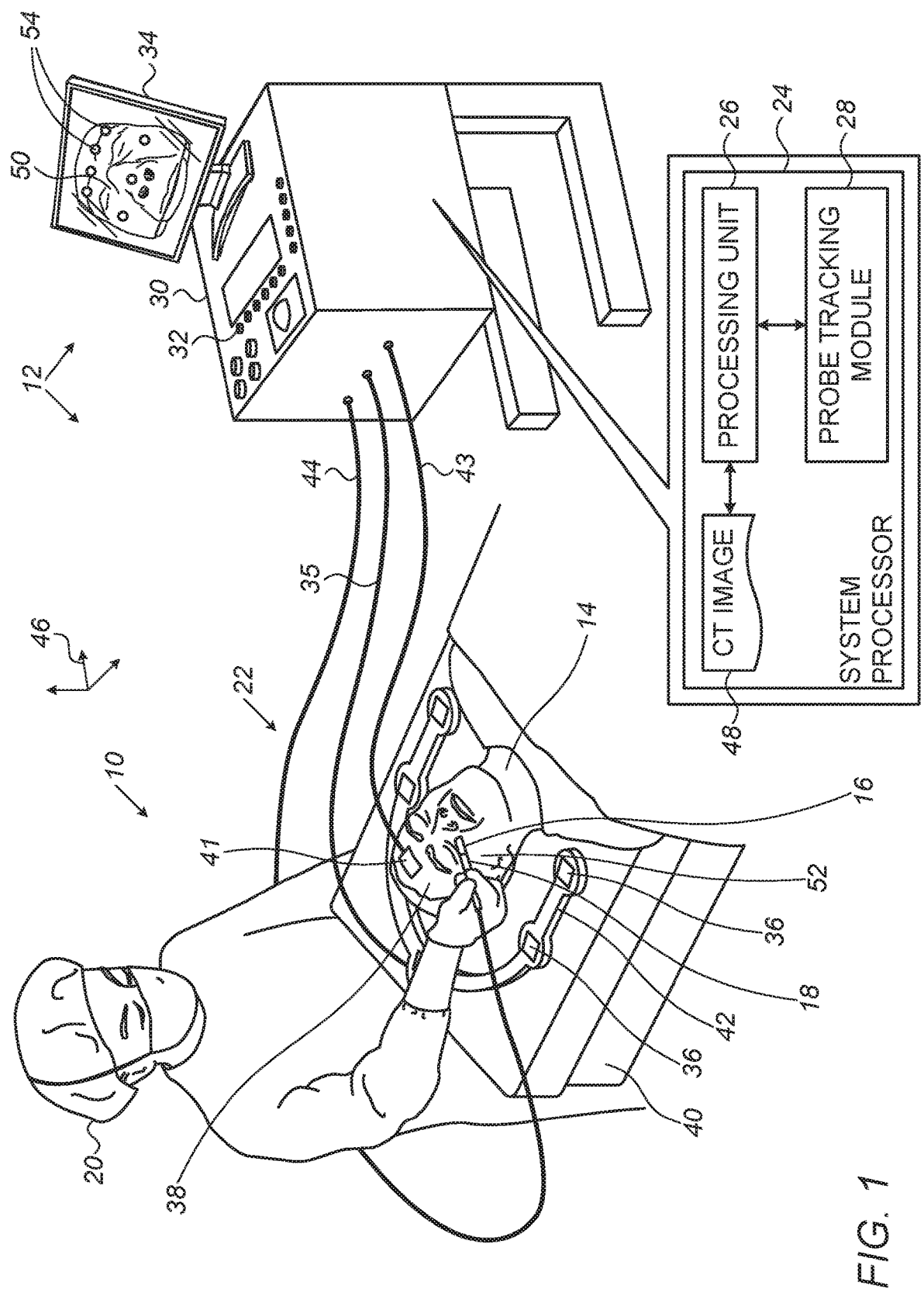
FIG. 1 is a schematic pictorial illustration of a medical apparatus, according with an embodiment of the invention.

Magnetic tracking systems are used for tracking instruments in invasive diagnostic and therapeutic procedures, such as image-guided surgery, using pre-acquired images, such as CT images, of the part of the body of the patient undergoing the procedure. In order for the tracking to be effective, frames of reference of the image and the tracking system have to be registered with each other. In a typical registration procedure between, for example, a CT image and a magnetic tracking system, the coordinates of a number of different anatomical points (referred to as landmarks) are marked in the CT image, and the coordinates of the same landmarks are acquired by the tracking system. Once pairs of such coordinate points have been acquired, a fitting process is applied in order to estimate the transformation, including scaling, rotation and translation, that best aligns, i.e., registers, the two sets of points. The fit may be computed, for example, using algorithms that are known in the art, such as cumulative distance metric or an iterative closest point (ICP) algorithm.

As an example, we will consider a procedure requiring tracking of an instrument used on a patient's head, such as an ear, nose, and throat (ENT) procedure. In such a procedure, the head of the patient is registered with the frame of reference of the tracking system. An example of such a registration procedure is provided in United States Patent Application Publication 2019/0046272. In the described procedure, a medical practitioner, such as a physician, positions the distal end of a probe comprising a magnetic tracking sensor at a preset number of landmark points on the patient's skin. The landmark points correspond to predetermined positions in the CT image. In the cited example, four initial landmark points, comprising a point below the tip of the patient's nose, the left and right sides of the patient's face besides the eyes, and a point between the eyes are used, and signals from tracking sensor are acquired at these points.

Once the signals from the tracking sensor have been acquired, the processor calculates respective position coordinates in the magnetic assembly frame of reference, so as to generate four ordered pairs of positions, each ordered pair having the form (tracking sensor position, CT position), with each pair referring to corresponding positions. The system processor uses these four ordered pairs to generate a preliminary registration, i.e., a transformation comprising scaling, translation and a rotation parameters, that aligns the CT coordinate system with that of the magnetic assembly.

The physician continues by positioning the distal end of the probe on the patient's skin at additional landmark points that he/she has defined. Each time signals are acquired, the processor uses the coordinates determined by the signals to update the transformation, using the new position as an addition to a source cloud of points.

For defining the landmark points, present systems guide the physician in the registration process by presenting a schematic image of a "generic" head on a screen viewed by the physician, with markers on the image indicating points to be touched. Actual patient features, however, may greatly differ from the generic head, making it difficult for the physician to decide where to touch the patient. In extreme cases, the difference may be so large as to make an accurate registration impossible.

The embodiments of the present invention that are described herein address this problem by providing a medical apparatus, which incorporates a position-tracking system, a registration tool with a position sensor, a display screen, and a processing unit. An accurate registration between the position-tracking system and a 3D image of the patient is enabled by generating a true and realistic two-dimensional (2D) image of the patient's body from the 3D image data, and guiding the registration procedure based on this 2D image, rather than simply using a generic, predefined image. This approach facilitates rapid convergence of the fitting process between the coordinate systems of the CT and the tracking system and leads to more accurate registration than in systems that are known in the art.

In the disclosed embodiments, the processing unit receives 3D image data of a part of the body of the patient, and generates a 2D image of the surface of the part of the body of the patient based on the 3D image data. The processing unit further renders the 2D image to the display screen, and superimposes, under guidance from the physician, onto the displayed 2D image icons indicating locations of respective landmarks on the surface of the part of the body. The physician touches with the registration tool, guided by these icons on the 2D image, the corresponding points on the patient's body and indicates to the processing unit which point he/she has touched. The processing unit receives the corresponding 3D position coordinates of the position sensor acquired by the position-tracking system from these points. Finally, the processing unit registers the frame of reference of the position-tracking system with the frame of reference of the 3D image data by relative translations and rotations of the two frames of reference, until the correlation between the 3D coordinates acquired by the position-tracking system and the coordinates of the 3D image data corresponding to the icons is maximized.

System Description

FIG. 1 is a schematic pictorial illustration of a medical apparatus 10, according with an embodiment of the invention. Apparatus 10 is used to register a magnetic position-tracking system 12 with an image, herein by way of example assumed to comprise a computerized tomography (CT) image 48, of a patient 14. Position-tracking system 12 is herein, by way of example, assumed to comprise a magnetic tracking system. The Carto® system, produced by Biosense Webster, of Irvine, Calif., uses a tracking system similar to that described herein to track the location and orientation of the distal tip of a probe inserted into or brought into the vicinity of a patient.

Position-tracking system 12 is used to track positions and orientations of one or more instruments, such as catheters or guidewires, that are inserted into patient 14 during a medical procedure performed on the patient. As is described below, position-tracking system 12 is also able to track the position and orientation of a registration probe 16 that is external to the patient. Probe 16 is fixedly connected to a handle 18 that may be held by a medical practitioner 20, typically a physician, during use of system 10. The combination of probe 16 and handle 18 form a rigid probe assembly 22 that facilitates the positioning by physician 20 of the probe to a desired location.

For clarity and simplicity in the following description, the medical procedure referred to above is assumed to comprise an invasive procedure on a nasal sinus of patient 14, so that medical apparatus 10 and magnetic position-tracking system 12 are assumed to be configured to operate in and around the region of the nasal sinus. However, systems 10 and 12 may alternatively be configured to operate in and around other regions of a patient, such as the thorax, kidneys or abdomen, and those having ordinary skill in the art will be able to adapt the description herein for such other regions. Furthermore, the principles of the present invention may be applied in conjunction with other types of tracking systems (not necessarily magnetic), as well as other sorts of 3D imaging modalities, such as MRI.

Tracking system 12 is operated by a system processor 24, comprising a processing unit 26 communicating with a probe tracking module 28. The function of module 28 is described below. System processor 24 may be mounted in a console 30, which comprises operating controls 32 that typically include a pointing device such as a mouse or trackball. Physician 20 uses operating controls 32 to transmit commands to system processor 24, which, as described below, is further used to present to the physician data and guiding imagery on a display screen 34.

System processor 24 typically comprises a programmable processor, which uses software stored in a memory of processing unit 26 to operate apparatus 10. The software may be downloaded to system processor 24 in electronic form, over a network, for example, or it may, alternatively or additionally, be provided and/or stored on non-transitory tangible media, such as magnetic, optical, or electronic memory. System processor 24 further stores digitized 3D CT image 48 of head 38 of patient 14, wherein the CT image has been acquired by a separate CT system (not shown), possibly at a different point in time. CT image 48 comprises, for each point in the image, its 3D coordinates, as well as the radiographic density of the image at each point, with the density typically given in Hounsfield units.

In order to track the instruments referred to above within patient 14, as well as to track probe 16, processing unit 26 uses probe tracking module 28 to operate, via a cable 35, a plurality of magnetic field generators 36, such as coils. In one embodiment, typically applicable if patient 14 is anesthetized and has a recumbent immobile head 38 on a bed 40, generators 36, as illustrated in FIG. 1, are fixed to a frame 42 placed on the bed, beside the patient's head. In an alternative embodiment (not shown), applicable if patient 14 is not anesthetized, generators 36 are fixed with respect to each other and to a frame attached to head 38 or to a chair in a physician's office. A three-axis reference coil 41 is fixed to head 38, and connected to processing unit 26 by a cable 43.

Generators 36 radiate alternating magnetic fields into and around head 38 of patient 14, and these fields generate signals in magnetic detectors in the instruments and in probe 16. The signals are conveyed back to processing unit 26 and probe tracking module 28, via a cable 44 connecting probe 16 to console 30. The processing unit and the module together analyze the signals to derive location and orientation coordinates of the instruments and probe 16 with respect to generators 36. Magnetic field generators 36 thus define a coordinate frame of reference 46 of magnetic tracking system 12.

Figure 2:
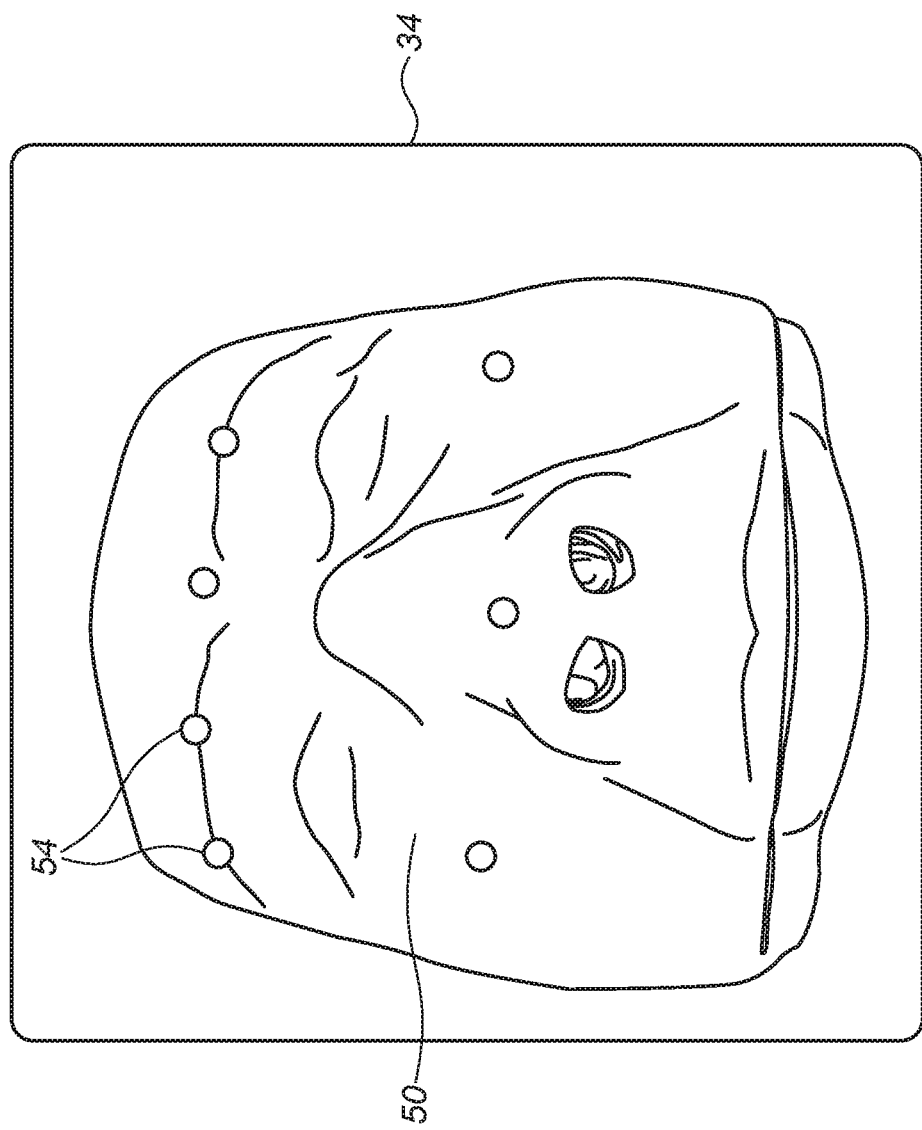
FIG. 2 is a schematic representation of a user interface screen, in accordance with an embodiment of the invention.
Figure 3:
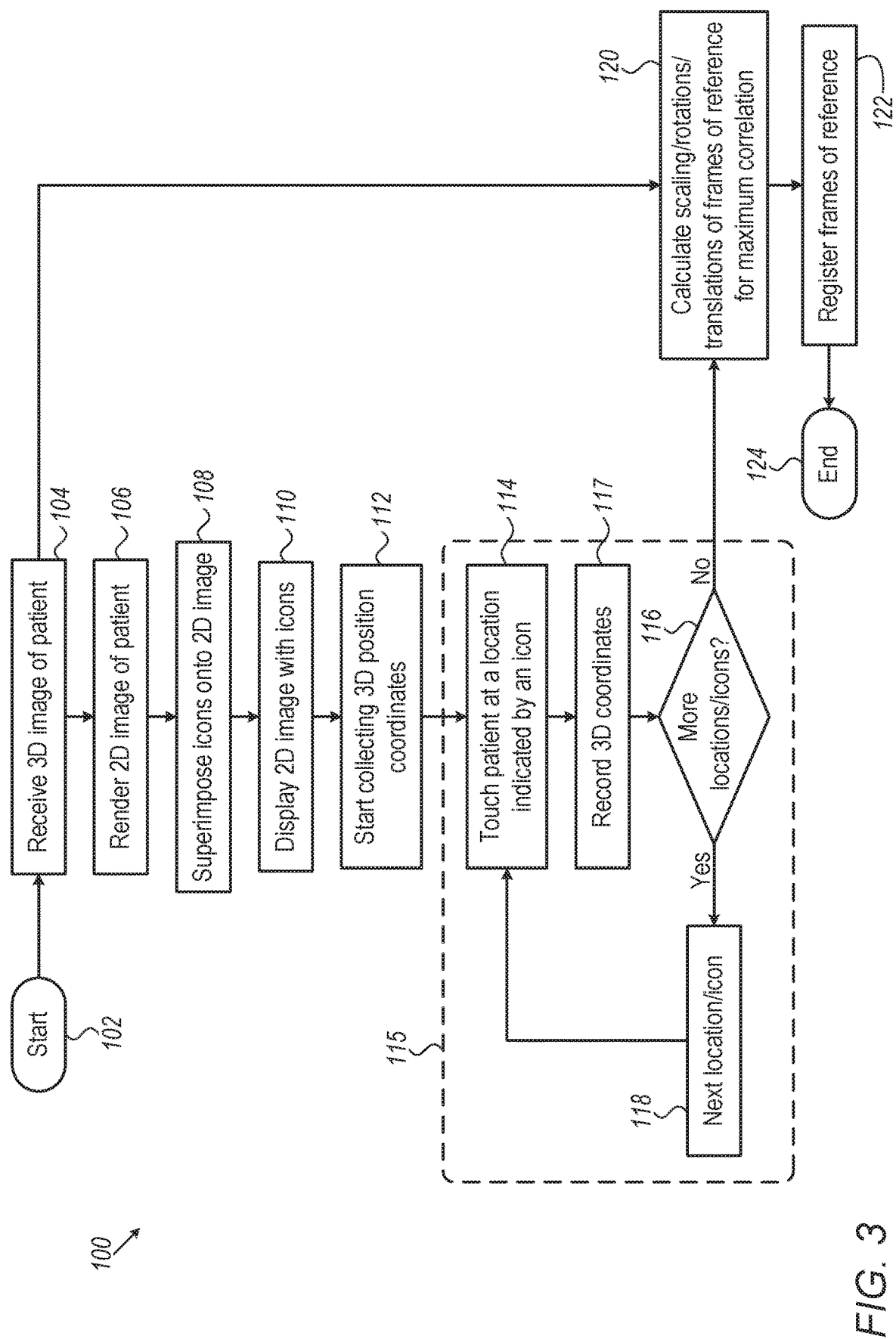
FIG. 3 is a flowchart that schematically illustrates a registration procedure between a 3D image and a position-tracking system, in accordance with an embodiment of the invention.

During the process of registration, and as further detailed in a flowchart in FIG. 3, processing unit 26 accesses 3D CT image 48 and renders it into a 2D image 50 on display screen 34. Processing unit 26 further superimposes icons 54 onto selected points on 2D image 50, typically corresponding to anatomical landmarks on the patient's face, as further detailed in FIG. 2. Physician 20 brings probe 16 into contact with a surface 52 of patient 14 (i.e., with the skin of the patient) at each point corresponding to an icon 54 in turn, and processing unit 26 records the 3D coordinates of the probe at each of these points. Using these recorded coordinates and the coordinates of the corresponding points in the frame of reference of CT image 48, processing unit 26 registers the frame of reference of position-tracking system 12 with the frame of reference of 3D CT image 48 by computing a transformation including relative scaling, rotations and translations of the two frames of reference. Typically, the transformation is found by a fitting process, which maximizes the correlation between the registered 3D coordinates of the probe and the 3D coordinates of CT image 48 corresponding to icons 54. For maximizing the correlation, processing unit 26 may use algorithms such as cumulative distance metric or an iterative closest point (ICP) algorithm, as will be further detailed in reference to FIG. 3.

Processing unit 26 may maximize the correlation after all 3D coordinate points corresponding to all icons 54 have been collected. Alternatively, processing unit 26 may start calculating the correlation with the first few tracked and recorded points (as is also described in the cited United States Patent Application Publication 2019/0046272), and then improves the correlation with every additional recorded point. In the iterative method, processing unit 26 may also estimate whether the 3D coordinates of each next point touched by probe 16 are sufficiently close to an expected location, and either indicate an acceptable proximity, for example by coloring the corresponding icon green, or an unacceptable distance by coloring the corresponding icon by red.

A communication between physician 20 and processing unit 26 is established in order to indicate which point on surface 52 is touched. For example, processing unit 26 may cause an icon 54 to flash on display screen 34, thus indicating to physician 20 the point he/she is expected to touch. Once physician 20 has touched this point, he/she indicates through controls 32 (for example, by pressing a key in the keypad or clicking the mouse) that the point has been touched. Alternatively, each icon 54 may be numbered using a numerical sequence, and physician 20 indicates through controls 32 which of the icons he/she has touched.

FIG. 2 is a schematic detail view of 2D image 50 as presented on display screen 34, in accordance with an embodiment of the invention. Image 50 has been rendered by processing unit 26 from 3D CT image 48, and is therefore a true and realistic image of a face of patient 14. For rendering image 50 from 3D CT image 48, processing unit 26 applies an algorithm, such as the marching cubes algorithm, to the CT image. The algorithm assigns a value of one to each point of CT image 48 at which the radiodensity in Hounsfield units is non-zero, and a value of zero to the points with a Hounsfield value of zero (corresponding to air). The algorithm proceeds through image 48, taking eight neighboring locations at a time (thus forming an imaginary cube), and determining the polygon needed to represent the part of the so-called isosurface that passes through this cube. (The isosurface is a surface that represents a boundary between the values of zero and one of the cube vertices in a linear approximation.) The individual polygons are then fused into a 3D surface, which is projected onto a plane corresponding to the plane of display screen 34.

Processing unit 26 has superimposed icons 54 on points on 2D image 50 corresponding to facial landmarks. Based on the rendering process, each icon 54 is automatically tied to a corresponding 3D coordinate in the CT frame of reference. Physician 20 may define the positions of icons 54 on image 50 by, for example, using controls 32 to move a cursor on display screen 34 to locations that he/she sees as appropriate, and then indicate these locations to processing unit 26 by a click of the mouse. In the present example, physician 20 has selected these locations in areas of the face that are relatively firm, i.e., that do not significantly compress under a mild pressure from probe 16. Such areas include, for example, the forehead, the tip of the nose, and protruding cheek bones. Alternatively or additionally, the positions of some or all of icons 54 may be selected automatically by processing unit 26.

FIG. 3 is a flowchart 100 that schematically illustrates a registration procedure between 3D image 48 and position-tracking system 12, in accordance with an embodiment of the invention. The registration procedure that is illustrated in flowchart 100 refers to the elements shown in FIGS. 1-2. Alternatively, the principles of this procedure may be applied in connection with other sorts of 3D images and tracking systems.

The procedure starts at a start step 102. In a 3D image step 104, 3D CT image 48 of the face of patient 14 is received by processing unit 26. In a rendering step 106, processing unit 26 renders 2D image 50 based on 3D CT image 48, as described in relation to FIG. 2. In a superimposition step 108, processing unit 26 superimposes icons 54, representing landmarks on the face of patient 14 onto image 50. In a display step 110, processing unit 26 displays image 50 together with icons 54 on display screen 34.

In a coordinate-collection start step 112, physician 20 starts the process of collection of 3D coordinates by touching the face of patient 14 with probe 16. The process now enters a loop 115, comprising a touch step 114, a recording step 117, a decision step 116, and a next icon step 118. In touch step 114, physician 20 touches the face of patient 14 with probe 16 in a location indicated by icon 54. The communication between physician 20 and processing unit 26 has been described in reference to FIG. 1, above, and will not be detailed further here. The 3D coordinates of probe 16 sensed by position-tracking system 12 are recorded by processing unit 26 in recording step 117. After recording the 3D coordinates, processing unit 26 determines in decision step 116 whether more locations need to be touched. In case the answer is affirmative, the next location (icon) is chosen, either by physician 20 or by processing unit 26, as described above, and the physician touches the next location in step 114.

Once all the required locations (icons) have been exhausted, the process exits from decision step 116 into a calculation step 120, in which processing unit 26 calculates the relative scaling, rotations and translations between the two frames of reference, typically so as to maximize a correlation between the 3D coordinates recorded in recording step 117 and the 3D coordinates of 3D image 48 that correspond to icons 54.

An example of an algorithm for maximizing the correlation between the two sets of 3D coordinates is provided by U.S. Pat. No. 7,855,723. The correlation is maximized by iteratively updating the scaling, rotation and translation coefficients in order to minimize a cumulative distance metric D, defined as $$D=\sqrt{\Sigma_i w_i d_i^2},$$

wherein $d_i$ is a three-dimensional Euclidian distance calculated between the respective $i^{th}$ points of the two sets of coordinates, and $w_i$ is an optional weight, describing, for instance, a confidence level that may be assigned to each point.

Alternatively or additionally, an iterative closest point (ICP) algorithm cited in the above-referenced United States Patent Application Publication 2019/0046272, may be used. The ICP algorithm is also based on minimizing the cumulative distance metric D, with an additional option of switching the points used for the pairs of the 3D points in order to further minimize the cumulative distance. The ICP algorithm, as applied to the described embodiment, can comprise the following steps:
1. Match each 3D coordinate point of position-tracking system 12 (points recorded in recording step 117) to the closest 3D coordinate point of 3D CT image 48, wherein closeness of a pair of points is determined by the 3D Euclidian distance $d_i$ between them.
2. Estimate the combination of scaling, rotation, and translation that will minimize the cumulative distance metric D. This step may also involve weighting points (i.e., assigning non-unity values to $w_i$) and rejecting outliers (i.e., rejecting point-pairs for which $d_i$ exceeds a pre-set threshold) prior to alignment. This step may be carried out, for example, by computing an initial estimate of the scaling, rotation, and translation over a small group of point-pairs, and then refining the estimate iteratively while incorporating additional point-pairs.
3. Transform the 3D coordinate points of position-tracking system 12 by using the obtained transformation of scaling, rotation, and translation.
4. Iterate the process back to step 1 by re-associating 3D coordinate points of position-tracking system 12 with 3D coordinate points of image 48. In case the re-association does not reduce the RMS distance metric, accept the last transformation as the coordinate transformation between the coordinate systems of position-tracking system 12 and the CT system.

As the process of maximizing the correlation may be iterative, a criterion for accepting a maximized correlation may be set by, for example, accepting a correlation as maximal, when a subsequent step of iteration increases the correlation (or reduces the cumulative distance metric D) by less than a predetermined threshold. Once the maximum correlation has been reached, the relative rotations and translations between the two frames of reference are saved in a registration step 122 as the registration between the frames. The process then ends in an end step 124.

In an alternative embodiment, as described above, wherein the correlation is calculated starting with the first few recorded 3D coordinates, calculation step 120 is moved inside loop 115 (not shown here).

Once the registration process is complete, physician 20 may proceed to perform an invasive procedure on patient 14 using system 10. For this purpose the physician inserts a probe (not shown in the figures), with a position sensor in or near its distal end, into the patient's head, for example into the sinus passages. Processor 24 tracks the position of the probe and registers the position relative to the CT image using the transformation found at step 122, in order to provide the physician with an accurate indication of the location of the probe relative to the patient's anatomy.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:
1. A method, comprising:
(a) receiving image data for a portion of a patient's body;
(b) rendering an image of the portion of the patient's body based on the image data;
(c) superimposing a plurality of icons onto the image at respective locations, each icon of the plurality of icons corresponding to a respective landmark of a plurality of landmarks on the portion of the patient's body;
(d) after superimposing the plurality of icons onto the image, receiving a plurality of position coordinates from a position-tracking system, each position coordinate of the plurality of position coordinates being acquired by the position-tracking system while a registration tool contacts a respective landmark of the plurality of landmarks; and (e) registering the image to the portion of the patient's body by correlating the plurality of position coordinates received from the position-tracking system to the respective locations of the plurality of icons superimposed onto the image.

2. The method of claim 1, the image data including three-dimensional (3D) image data for the portion of the patient's body.

3. The method of claim 1, the image data including at least one of a computerized tomography (CT) image or magnetic resonance imaging (MRI) data.

4. The method of claim 1, the portion of the patient's body including a head of the patient's body, the image including an image of a facial surface of the head.

5. The method of claim 1, rendering the image of the portion of the patient's body including rendering the image of the portion of the patient's body to a display screen, superimposing the plurality of icons onto the image including superimposing the plurality of icons on the display screen.

6. The method of claim 1, the plurality of icons including a plurality of circles.

7. The method of claim 1, the plurality of icons including a plurality of colored icons.

8. The method of claim 1, the plurality of icons including a plurality of numbered icons.

9. The method of claim 1, the plurality of landmarks including at least one anatomical landmark.

10. The method of claim 1, further comprising tracking a position of a tool relative to the portion of the patient's body.

11. A system, comprising:
(a) a registration tool;
(b) a position-tracking subsystem; and
(c) a processor, the processor being configured to:
(i) receive image data for a portion of a patient's body,
(ii) render an image of the portion of the patient's body based on the image data,
(iii) superimpose a plurality of icons onto the image at respective locations, each icon of the plurality of icons corresponding to a respective landmark of a plurality of landmarks on the portion of the patient's body,
(iv) receive a plurality of position coordinates from the position-tracking subsystem after superimposing the plurality of icons onto the image, each position coordinate of the plurality of position coordinates being acquired by the position-tracking system while the registration tool contacts a respective landmark of the plurality of landmarks, and
(v) register the image to the portion of the patient's body by correlating the plurality of position coordinates received from the position-tracking system to the respective locations of the plurality of icons superimposed onto the image.

12. The system of claim 11, the portion of the patient's body including a head of the patient's body, the image including an image of at least one facial feature of the head.

13. The system of claim 11, the plurality of icons including a plurality of circles.

14. The system of claim 11, the plurality of icons including a plurality of colored icons.

15. The system of claim 11, the plurality of icons including a plurality of numbered icons.

16. A computer software product comprising a tangible non-transitory computer-readable medium in which program instructions are stored, which instructions, when read by a processor, cause the processor to:
(a) receive image data for a portion of a patient's body;
(b) render an image of the portion of the patient's body based on the image data;
(c) superimpose a plurality of icons onto the image at respective locations, each icon of the plurality of icons corresponding to a respective landmark of a plurality of landmarks on the portion of the patient's body;
(d) receive a plurality of position coordinates from a position-tracking system after superimposing the plurality of icons onto the image, each position coordinate of the plurality of position coordinates being acquired by the position-tracking system while a registration tool contacts a respective landmark of the plurality of landmarks; and
(e) register the image to the portion of the patient's body by correlating the plurality of position coordinates received from the position-tracking system to the respective locations of the plurality of icons superimposed onto the image.

17. The computer software product of claim 16, the portion of the patient's body including a head of the patient's body, the image including an image of at least one facial feature of the head.

18. The computer software product of claim 16, the plurality of icons including a plurality of circles.

19. The computer software product of claim 16, the plurality of icons including a plurality of colored icons.

20. The computer software product of claim 16, the plurality of icons including a plurality of numbered icons.

* * * * *